US011202615B2

(12) United States Patent
Sørensen et al.

(10) Patent No.: US 11,202,615 B2
(45) Date of Patent: *Dec. 21, 2021

(54) METHOD FOR REPLACING A ROTATIONAL AXIS DECODER IN A SCANNING SYSTEM

(71) Applicant: 3SHAPE A/S, Copenhagen K (DK)

(72) Inventors: Thomas Sangild Sørensen, Aarhus C (DK); Sami Brandt, Bunkeflostrand (SE)

(73) Assignee: 3SHAPE A/S, Copenhagen K (DK)

( * ) Notice: Subject to any disclaimer, the term of this patent is extended or adjusted under 35 U.S.C. 154(b) by 80 days.

This patent is subject to a terminal disclaimer.

(21) Appl. No.: 16/829,670

(22) Filed: Mar. 25, 2020

(65) Prior Publication Data

US 2020/0315568 A1    Oct. 8, 2020

Related U.S. Application Data

(63) Continuation of application No. 16/466,694, filed as application No. PCT/EP2017/081447 on Dec. 5, 2017, now Pat. No. 10,709,412.

(51) Int. Cl.
| | |
|---|---|
| G06K 9/00 | (2006.01) |
| A61B 5/05 | (2021.01) |
| A61B 6/00 | (2006.01) |
| G06T 7/292 | (2017.01) |
| A61B 5/11 | (2006.01) |

(Continued)

(52) U.S. Cl.
CPC ............. *A61B 6/584* (2013.01); *A61B 5/117* (2013.01); *A61B 5/1127* (2013.01); *A61B 6/032* (2013.01); *A61B 6/4085* (2013.01); *A61B 6/547* (2013.01); *G06T 7/292* (2017.01)

(58) Field of Classification Search
USPC ................ 382/103, 100, 106–107, 128–134, 382/154–155, 162, 168, 173, 181, 189, 382/199, 219, 224, 232, 254, 274, 276, 382/286–291, 305, 312; 1/1; 378/4, 21,
(Continued)

(56) References Cited

U.S. PATENT DOCUMENTS

| | | | |
|---|---|---|---|
| 6,050,724 A | 4/2000 | Schmitz et al. | |
| 6,079,876 A | 6/2000 | Schuetz | |

(Continued)

FOREIGN PATENT DOCUMENTS

| | | | |
|---|---|---|---|
| WO | 2016139347 A1 | 9/2016 | |
| WO | 2016156150 A1 | 10/2016 | |

OTHER PUBLICATIONS

International Search Report (PCT/ISA/210) dated Apr. 6, 2018, by the European Patent Office as the International Searching Authority for International Application No. PCT/EP2017/081447.

*Primary Examiner* — Seyed H Azarian
(74) *Attorney, Agent, or Firm* — Buchanan Ingersoll & Rooney P.C.

(57) ABSTRACT

A method for determining the position and/or orientation of at least one sensor system relative to the base structure of a scanning system during scanning of an object, the method includes obtaining one or more tracking images using one or more cameras, where the cameras are in a fixed position with respect to the sensor system; and determining from the one or more tracking images the position and/or orientation of the sensor system relative to the base structure at a given time.

12 Claims, 6 Drawing Sheets

(51) Int. Cl.
*A61B 5/117* (2016.01)
*A61B 6/03* (2006.01)

(58) Field of Classification Search
USPC ............ 378/63, 426; 600/424, 426; 433/29; 348/65
See application file for complete search history.

(56) References Cited

U.S. PATENT DOCUMENTS

| | | | |
|---|---|---|---|
| 6,379,041 B1 | 4/2002 | Schuetz et al. | |
| 2013/0093866 A1* | 4/2013 | Ohlhues | G01C 11/04 348/65 |
| 2014/0107390 A1* | 4/2014 | Brown | A61N 5/107 600/1 |
| 2014/0316257 A1* | 10/2014 | Woerlein | A61B 5/061 600/424 |
| 2015/0243025 A1* | 8/2015 | Berlinger | A61B 6/486 382/131 |
| 2017/0065832 A1* | 3/2017 | Berlinger | A61B 6/5264 |
| 2019/0343478 A1 | 11/2019 | Sørensen et al. | |

* cited by examiner

METHOD FOR REPLACING A ROTATIONAL AXIS DECODER IN A SCANNING SYSTEM

CROSS-REFERENCE TO RELATED APPLICATIONS

This application is a continuation of U.S. Ser. No. 16/466,694, filed on Jun. 5, 2019, which is a national stage application of PCT/EP2017/081447, filed on Dec. 5, 2017, and which claims the priority of Danish Patent Application PA201670959, filed on Dec. 5, 2016. The subject matter of U.S. Ser. No. 16/466,694; PCT/EP2017/081447; Danish Patent Application PA201670959.

FIELD OF THE INVENTION

This invention generally relates to a method and system for determining the movement of a sensor system in relation to scanned stationary base of a scanning system. More specifically, the invention describes a method and system for determining the rotational movement of the sensor system of a scanning system relative to the stationary base of the scanning system. In particular embodiments, disclosed herein is a method and system for determining the rotational movement of an x-ray source and sensor in a dental CBCT scanning system without the use of a physical motor encoder.

BACKGROUND

Mechanical motor encoders are well known in the art, and come in many varieties. A rotary encoder, also called a shaft encoder, is an electro-mechanical device that converts the angular position or motion of a shaft or axle to an analog or digital code. They are therefore used to determine the amount of rotation of a shaft in a rotating machine.

In 2D and 3D scanners, such as optical scanners and x-ray machines, one or more sensors and/or radiation sources typically move or rotate around the object being imaged. For example, in a Cone Beam Computed Tomography (CBCT) scanner, an x-ray source and x-ray sensor are mounted on a ring, which rotates around a person being scanned. When reconstructing the volumetric 3D x-ray image, it is important to know the geometry of the scanner with respect to the patient. For this reason, the patient is typically fixated using a head band to keep the patient from moving during an exposure, and rotary encoders are typically used to determine the position of the x-ray source and sensor relative to the patient.

U.S. Pat. No. 6,079,876 discloses an X-ray system having a position indicator arranged separate from the X-ray apparatus onto which a camera is directed for determining the positions of the X-ray source and the X-ray receiver.

U.S. Pat. No. 6,050,724 discloses a method of position detection in X-ray imaging, wherein the detector device is mounted on the X-ray apparatus and the indicator device is provided so as to be stationary on the object to be examined.

U.S. Pat. No. 6,379,041 discloses an X-ray apparatus with an arrangement for determining intrinsic imaging parameters including X-ray-positive marks which are allocated to the X-ray source and which are in the path of an X-ray beam emanating from the X-ray source, these marks following displacement of the X-ray system.

However, it remains to disclose a cone beam computed tomography system wherein physical motor encoders are not needed to determine the movement of the source and sensor in a scanning system.

SUMMARY

Disclosed is a method for determining the position and/or orientation of at least one sensor system relative to the base structure of a scanning system during scanning of an object, the method comprising:
  obtaining one or more tracking images using one or more cameras, where the cameras are in a fixed position with respect to the sensor system; and
  determining from the one or more tracking images the position and/or orientation of the sensor system relative to the base structure at a given time.

In this way, it is possible to determine the movement of the sensor systems with respect to the base structure of the scanner. Since the movement of the sensor systems has been determined, there is no need for a physical motor encoder.

In some embodiments, a tracking element is attached in a fixed position with respect to the base structure of the scanning system, the tracking element comprising one or more fiducial markers in a known configuration;
  the tracking images are images taken of the tracking element;
  the tracking images are processed to identify the position of the one or more fiducial markers in a plurality of the tracking images;
  the identified position of the fiducial markers is used to determine the position of the tracking element relative to the sensor system at a given time; and
  the determined position of the tracking element relative to the sensor system at a given time is used to determine the movement of the sensor system relative to the base structure of the scanning system scanned during the acquisition of medical images.

Since the tracking element is fixed to the scanning base structure, the determined relative position of the tracking element relative to the sensor system also defines the position of the sensor system with respect to the scanner base structure at any given time.

In some embodiments, a tracking element is attached to the object being scanned, the tracking element comprising one or more fiducial markers in a known configuration;
  the tracking images are images taken of the tracking element;
  the tracking images are processed to identify the position of the one or more fiducial markers in a plurality of the tracking images;
  the identified position of the fiducial markers is used to determine the position of the tracking element at a given time; and
  the determined position of the tracking element at a given time is used to determine the movement of the sensor system relative to the base structure of the scanning system during the acquisition of medical images.

The object being scanned may be stationary with respect to the scanner base structure. In this case, determining the relative movement of the sensor system with respect to the tracking element is equivalent to determining the relative the scanner base structure. However, if the object being scanned has some movement during scanning, this is not a precise determination. This could for example be the case, if the object being scanned is a person, and the person has not been physically fixated with respect to the scanner base structure. However, depending on the needed accuracy of the determined movement of the sensor system relative to the scanner base structure, this movement of the person may be considered negligible. For example, in a CBCT system, the sensor system rotates around the patient, with the distance between the source and sensor being on the order of 1 m-1.5 m. In this instance, movement of the patient on the order of mm or cm may be considered negligible with respect to the rotational movement of the sensor system around the person being scanned. In some cases, the CBCT system will have a default "home" position, that the x-ray source and sensor can return to automatically or if prompted by a user.

In some embodiments, the tracking images are taken of the object being scanned;
  the tracking images are processed to identify common features of the object being scanned in a plurality of the tracking images; and
  the identified common features are used to determine the position and/or orientation of the object relative to the cameras at a given time; and
  the determined position and/or orientation of the object relative to the cameras at a given time is used to determine the movement of the sensor system relative to the scanner base structure during the acquisition of medical images.

In this way, intrinsic features of the object being scanned may be used as identifying features, which can be recognized in each tracking image using a computer processor. The movement of the sensor systems with respect to the object being scanned during the acquisition of medical images can then be determined from the movement of the common features between tracking images.

In some embodiments, the tracking element comprises predefined information in the form of at least one fiducial marker, such as a plurality of fiducial markers in a predefined pattern, size, shape and/or colour.

When the placement, size, shape and/or colour of the fiducial markers are already known with very high accuracy before any images are taken, it is possible to determine with very high accuracy the movement of the tracking element between images.

In order to determine the orientation and position of the tracking element, image analysis algorithms can be used. For example, if the fiducial markers are in the form of dots of a known size, the algorithms can be used to detect where there are dots and what size they have. The method used may for example be principal component analysis (PCA), although other methods are also possible and known to the person skilled in the art.

Since the fiducial markers have a known size, shape and/or predefined pattern on the tracking element, once the size, shape and position of each found dot is determined, a mask comprising the known predefined pattern of the fiducial markers can by loaded from a database, be overlaid on the tracking image, and the fit of the tracking image to the mask can be determined, thereby finding the orientation and position of the tracking element.

In some embodiments, there may be more than one camera, such as two cameras or three cameras for recording the movement of the tracking element. The reason for this, is that if only one camera is used, it is difficult to unambiguously determine how far away from the camera the fiducial marker is. If two cameras are used, it is difficult to unambiguously determine the position of the tracking element in a direction that is parallel to a line connecting the two cameras. If, on the other hand, three cameras are used, possibly but not necessarily, placed for example at the points of an equilateral triangle, the position of the tracking element in all three dimensions can be unambiguously determined.

Determining the position and orientation of the tracking element using three cameras, can be accomplished for example by having the images from the three cameras time stamped so that at each time t, there are three images taken of the element, recognizing the fiducial markers in each image, determining a best fit to the known predefined pattern of the fiducial markers on the tracking element in each image, determining the position and orientation of the tracking element in each of the three images of the tracking element at each time stamp, and computing a weighted average of the position and orientation of the tracking element from the three images.

In some embodiments, determining the position and orientation of the tracking element at each time stamp comprises:
  recognizing a plurality of the individual fiducial markers in each tracking image;
  using classification of the indices of the fiducial markers; and
  matching the known pattern of the fiducial markers on the tracking element to the pattern of the fiducial markers on the tracking image using the classification of the indices of the fiducial markers.

Matching the known pattern of the fiducial markers may for example be accomplished using a computer device, where the tracking images are loaded, and the fiducial markers are recognized and/or segmented in the tracking images. Then, the position of the fiducial markers in the tracking image are indexed, and the index of the fiducial markers in the tracking image are compared to the known index of the fiducial markers on the tracking element. Since the distance between the fiducial markers on the tracking element is known, the distances between the fiducial markers in the tracking images can be compared to the known distances, and known mathematical algorithms can be used to determine the position and rotation of the tracking element in the tracking images.

In some embodiments, the camera position and rotation of each camera is calibrated or determined;
  the intrinsic parameters such as the focal length, skew, principal point and lens distortion are calibrated or determined for each camera;
  the tracking images from the three cameras are acquired simultaneously such that at each time t, there are three images taken of the tracking element;
  the fiducial markers are recognized in each tracking image and the position of each fiducial marker is determined directly in the camera co-ordinate frame;
  the position and/or orientation of the tracking element from the three images is determined using a cost function to minimise the difference in the determined position of the fiducial markers in each of the tracking images.

Since extrinsic parameters of the cameras are known (i.e. the position and rotation of the cameras with relation to the sensor system(s)), and the fiducial markers are recognized in each image and the position of the fiducial markers are determined directly in the co-ordinate frame of the camera, the determination of the position and rotation of the tracking element relative to the sensor system(s) will be more accurate.

In some embodiments, the tracking element may have only one fiducial marker, but preferably should have a plurality of fiducial markers on its surface, for example in the form of dots or circles. There may be any number of fiducial markers, for example more than 10, more than 100, more than 200 or more than 400 dots. Preferably there should be enough dots to make it simple to find the position and size of the dots, but not so many that it would take too much processing time.

In some embodiments, there are asymmetrical features on the tracking element or the tracking element itself is asymmetrical. In principle, it is possible to determine the position and orientation of the tracking element even if the fiducial markers are all placed in a completely symmetrical pattern. In this case, it would be assumed that the tracking element has moved the shortest possible distance that is consistent with the pattern of the fiducial markers, between each time stamp. However, if the fiducial markers are placed asymmetrically, or if the tracking element itself is asymmetrical, there is no ambiguity in when overlaying the mask of the known predefined pattern with the image of the tracking element.

In some embodiments, the object being scanned is assumed to be in a fixed positional relationship with respect to the base of the scanner, and the position and orientation of the tracking element is fixed with respect to the base of the scanner. In this manner, it is possible to determine the movement of the sensor system(s) with respect to the object being scanned, by determining the movement of the sensor system(s) with respect to the tracking element. In this way, since the object being scanned is assumed to be in a fixed positional relationship with respect to the base of the scanner, the determined movement of the sensor system(s) can be used similarly to how a physical motor encoder would normally be used. In these embodiments, the geometry of the scanner structure defines a coordinate system. For example with the origin at the centre of the camera structure. This coordinate system can be said to define the camera space. Another coordinate system can be said to define the object space, with the origin of the object space coordinate system placed for example at the centre of the tracking element. Since the tracking element position is fixed with respect to the scanner structure, the relationship between the camera space and the object space can be calculated at all times. A third coordinate system can be said to define the sensor system space. This coordinate system can have the origin for example at the centre of the sensor. Since the sensor system moves with respect to the scanner structure, the sensor system space will move with respect to the object space during scanning. Determining this relative movement will then yield the movement of the sensor system, in an analogous way to how a motor encoder will typically be used.

In general, as the sensor system rotates around the object being scanned, the 3D representation of the object will typically be determined in real time. For example, during dental imaging in a CBCT scanner, the scanner rotates around the patient's head, obtaining up to perhaps several hundred or thousand distinct images. The scanning software collects the data and reconstructs it, producing what is termed a digital volume composed of three-dimensional voxels anatomical data that can then be manipulated and visualized. The volumetric reconstruction techniques are well known in the art. The movement of the scanner with respect to the object can then be determined, since the object, in this case the patient, can be considered to be stationary with respect to the sensor system, the motion of the object space with respect to the scanner space can be determined for example by comparing the position of a certain feature or features in a subset of the images.

In some embodiments, the tracking element is attached to the object being scanned. In these embodiments, the cameras should have a fixed position and orientation relative to the sensor systems. In this way, the relative movement between the object being scanned and the sensor system(s) can be determined, even if there is some movement of the object. In this case it can in some situations be necessary to have a fail-safe mechanism, either mechanical or implemented in the control software of the scanner, so that movements of the object that are very large does not result in erroneous scans, or equipment malfunction.

In some embodiments, the tracking element and cameras define an axis of rotation of the scanner relative to the object being scanned. Therefore, it is possible to determine the rotational movement of the scanner with respect to the object being scanned.

In some embodiments, the determination of the position and/or orientation of the sensor system relative to the tracking element at a given time is used to replace a physical motor encoder. This makes the design of the scanner simpler, and less expensive to produce.

In some embodiments, the sensor system(s) comprises a cone beam computed tomography (CBCT) scanner, and the object being scanned is a person. The CBCT scanner uses an x-ray source and sensor and computer software to calculate a 3D volumetric model of at least a part of a patient's head, typically parts or all of one or both of the jaws. In these embodiments, the tracking element may for example be attached to a headband, which can be placed on the patient's head. It is an advantage if the headband is adjustable, since it should be possible to securely attach the headband to patients with different head sizes such as children and adults, with limited risk of the headband moving during the exposure time.

Since the cameras are already present to take tracking images of the object/patient being scanned, in order to track any movement during exposure, it is cost effective to use the same system instead of a physical rotational axis/motor encoder.

In some embodiments, the geometry of the scanner structure defines a coordinate system. For example, with the origin at the centre of the scanner base structure. This coordinate system can be said to define the scanner base space. Another coordinate system can be said to define the object space, with the origin of the object space coordinate system placed for example at the centre of the tracking element. Another coordinate system can be said to define the sensor system space, with the origin fixed for example at the centre of the sensor plate. A further coordinate system can be said to define the camera space, with the origin of the camea space being at the centre of the camera structure. The camera space may be considered to be stationary with respect to the moving sensor system. Since the geometry of the scanner system is known, it is possible to relate the stationary scanner base space with the moving sensor system space. This relationship can then be used to determine the amount of movement, for example rotation, of the sensor system coordinate system with respect to the stationary scanner structure. This can in turn be used as a substitute for a motor encoder, for example instead of a rotational axis encoder.

In some embodiments, there may be a default starting position of the sensor system, where the relationship between the sensor system and the scanner structure is calibrated. The scanner may revert to this default starting position before beginning each scan. In this way, it is only necessary to determine the relative movement of the sensor system with respect to the object being scanned, or the scanner structure. Any large movement, for example if a person is being scanned and they move outside the scannable area of the scanning system, the sensor system may revert back to the default starting position.

In one aspect disclosed herein is a system for obtaining x-ray images of at least a part of a person, the system comprising:
A stationary scanning base;
An x-ray sensor and an x-ray detector movably connected to the scanning base;
A tracking element and at least one camera for acquiring images of the tracking element during scanning of the person;
wherein the tracking element is in a fixed positional relationship with the scanning base.

In some embodiments, the system does not comprise a physical motor encoder.

In some embodiments, the rotational movement of the at least one sensor system with respect to the object being scanned can be determined without a physical motor encoder.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

Figure 1:
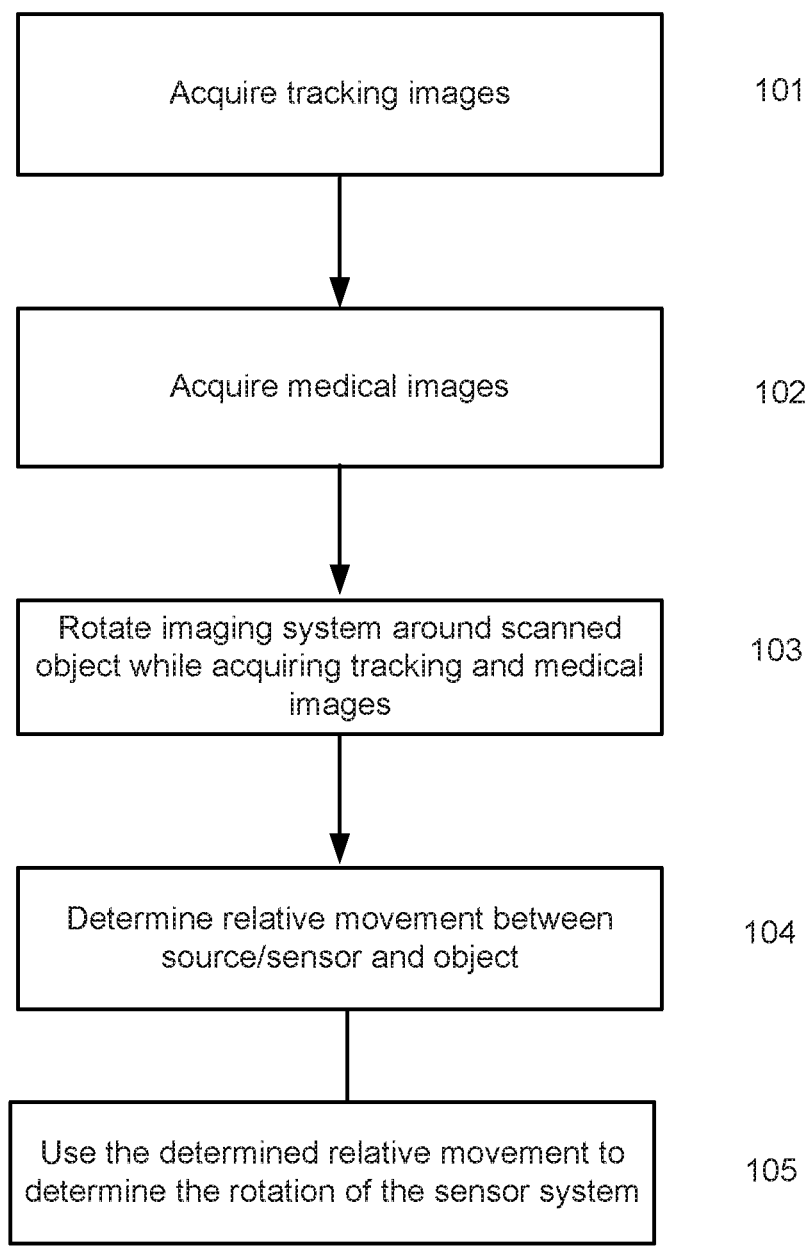
FIG. 1 shows a flowchart of a method according to an aspect of the invention

FIG. 1 shows a flowchart illustrating a method according to one aspect of the invention. In step 101, tracking images of a tracking element are taken using one or more optical cameras. The tracking element is attached to the object being scanned. The object may for example be a person. In step 102, medical images of an object to be scanned are taken using a sensor system, the sensor system comprising a radiation source and sensor. The radiation source and sensor may for example be an x-ray source and an x-ray sensor, for example as part of a CBCT system. The radiation source and sensor may for example be attached to a movable ring. Acquiring the tracking images may be started before or at the same time as the start of the acquiring of the medical images. In step 103, the radiation source and sensor are rotated around the object to be scanned, while tracking and medical images are acquired. In step 104, a computer processor determines the relative movement between the sensor system and the object being scanned. In step 105, the computer processor uses the determined relative motion between the sensor system and the object being scanned to determine the rotation of the sensor system, under the approximation that the object has not moved. Of course, in the case of a person being scanned, some movement is to be expected. However, for determining the rotational angle of the movable ring, small movements of the person may be considered negligible compare to the rotational movement of the sensor system.

Figure 2:
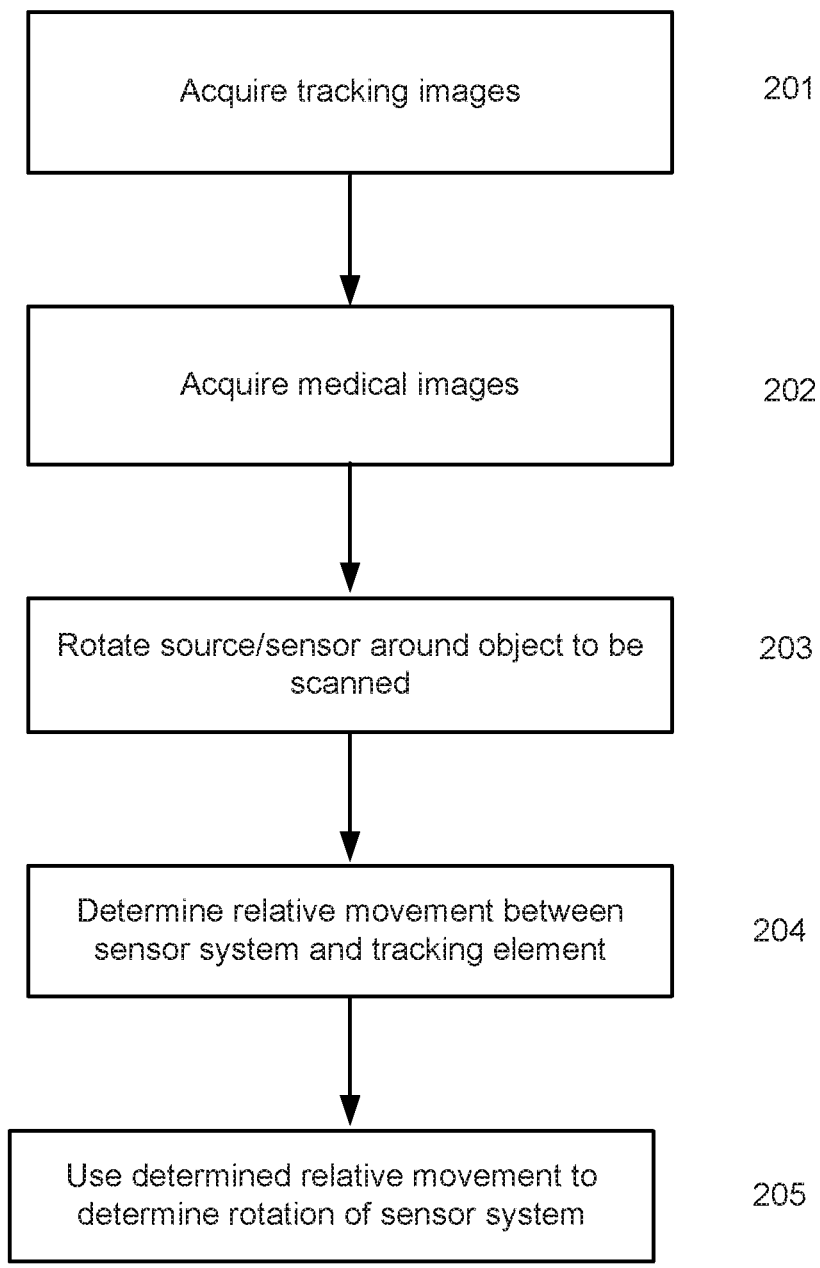
FIG. 2 shows a flowchart of a method according to another aspect of the invention

FIG. 2 shows a flowchart illustrating a method 200 according to one aspect of the invention. In step 201, tracking images of a tracking element are taken using one or more optical cameras. The tracking element is non-movably attached to the scanning system, i.e. the tracking element does not move relative to the base of the scanning system while the scanning system is in operation. In step 202, medical images of an object to be scanned are taken using a sensor system, the sensor system comprising a radiation source and sensor. The radiation source and sensor may for example be an x-ray source and an x-ray sensor, for example as part of a CBCT system. The radiation source and sensor may for example be attached to a movable ring. Acquiring the tracking images may be started before or at the same time as the start of the acquiring of the medical images. In step 203, the radiation source and sensor are rotated around the object to be scanned, while tracking and medical images are acquired. In step 204, a computer processor determines the relative movement between the sensor system and the tracking element. In step 205, the computer processor uses the determined relative motion between the sensor system and the tracking element to determine the rotation of the sensor system.

Figure 3:
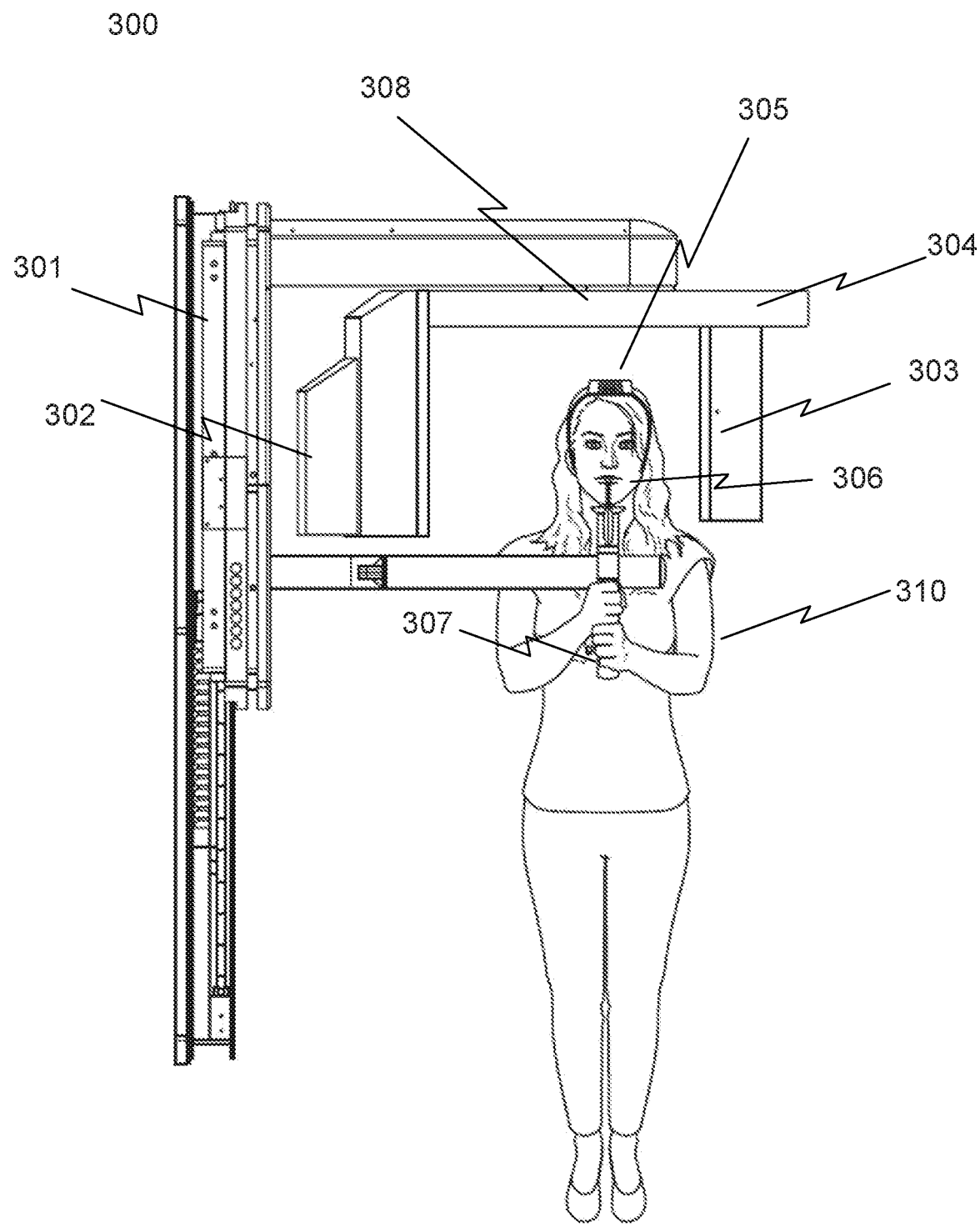
FIG. 3 shows a front view of a scanning system according to an aspect of the invention.

FIG. 3 shows a front view of a scanning system 300 according to one aspect of the invention. The scanning system comprises a scanner base structure 301, which may be attached to a wall. The scanning system further comprises a radiation source 302, a radiation sensor 303, the radiation source and sensor being attached to or part of a movable ring 304. A tracking element 305 is attached to the object being scanned, in this case a person 310. The scanning system may also comprise a chin rest 306 and a handle 307. The scanner base 301 also comprises at least one camera 308, placed so that it has a clear view of the tracking element 305. The camera(s) 308 are attached to the movable ring 304, so that the camera(s) are in a fixed spatial relationship with the radiation sensor 303 and/or radiation source 302.

An integrated or external computer processor (not shown) may also be considered a part of the scanning system.

Figure 4:
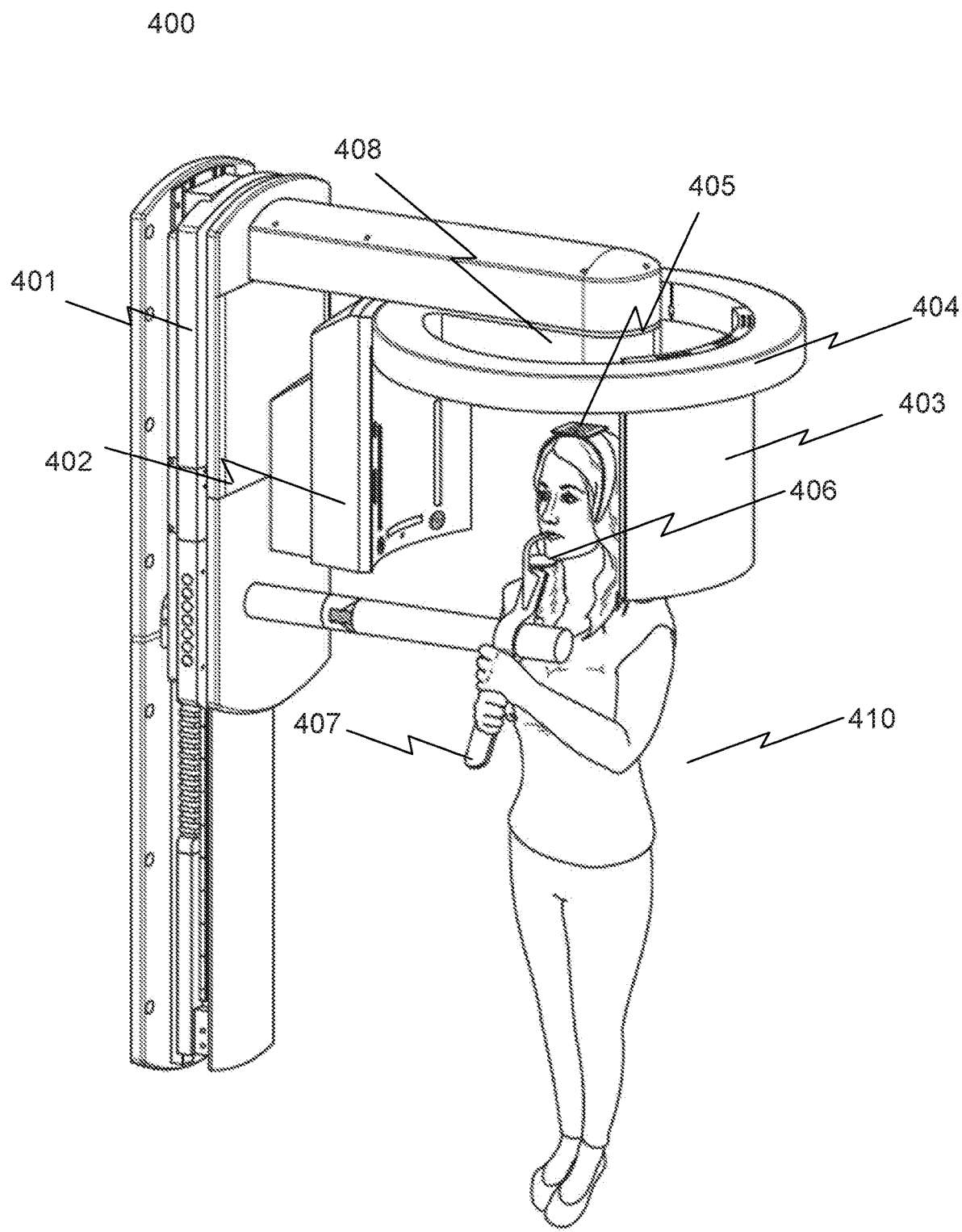
FIG. 4 shows an angled front view of a scanning system according to an aspect of the invention.

FIG. 4 shows an angled front view of the scanning system 400 according to one aspect of the invention. The scanning system comprises a scanner base structure 401, which may be attached to a wall. The scanning system further comprises a radiation source 402, a radiation sensor 403, the radiation source and sensor being attached to or part of a movable ring 404. A tracking element 405 is attached to the object being scanned, in this case a person 410. The scanning system may also comprise a chin rest 406 and a handle 407. The scanner base 401 also comprises at least one camera 408, placed so that it has a clear view of the tracking element 405. The camera(s) 408 are attached to the movable ring 404, so that the camera(s) are in a fixed spatial relationship with the radiation sensor 403 and/or radiation source 402. An integrated or external computer processor (not shown) may also be considered a part of the scanning system.

Figure 5:
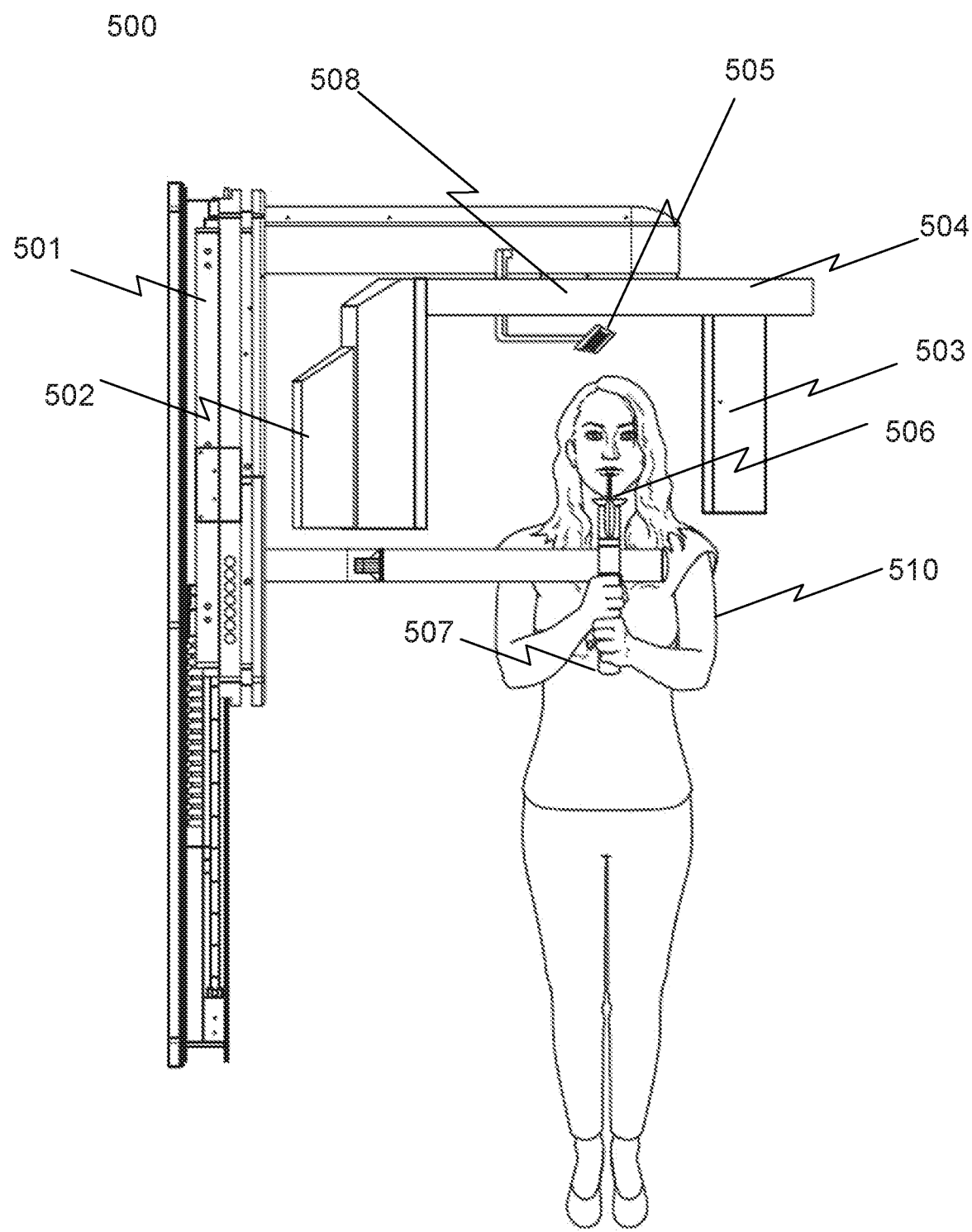
FIG. 5 shows a scanning system according to an aspect of the invention.

FIG. 5 shows a scanning system 500 according to one aspect of the invention. The scanning system comprises a scanner base structure 501, which may be attached to a wall. The scanning system further comprises a radiation source 502, a radiation sensor 503, the radiation source and sensor being attached to or part of a movable ring 504. A tracking element 505 is attached to the scanner base. The scanning system may also comprise a chin rest 506 and a handle 507. The scanner base 501 also comprises at least one camera 508, placed so that it has a clear view of the tracking element 505. The scanner system 500 is configured to scan an object, in this case a person 510. The camera(s) 508 are attached to the movable ring 504, so that the camera(s) have a fixed spatial relationship with the radiation source 502 and/or the radiation sensor 503. An integrated or external computer processor (not shown) may also be considered a part of the scanning system.

Figure 6:
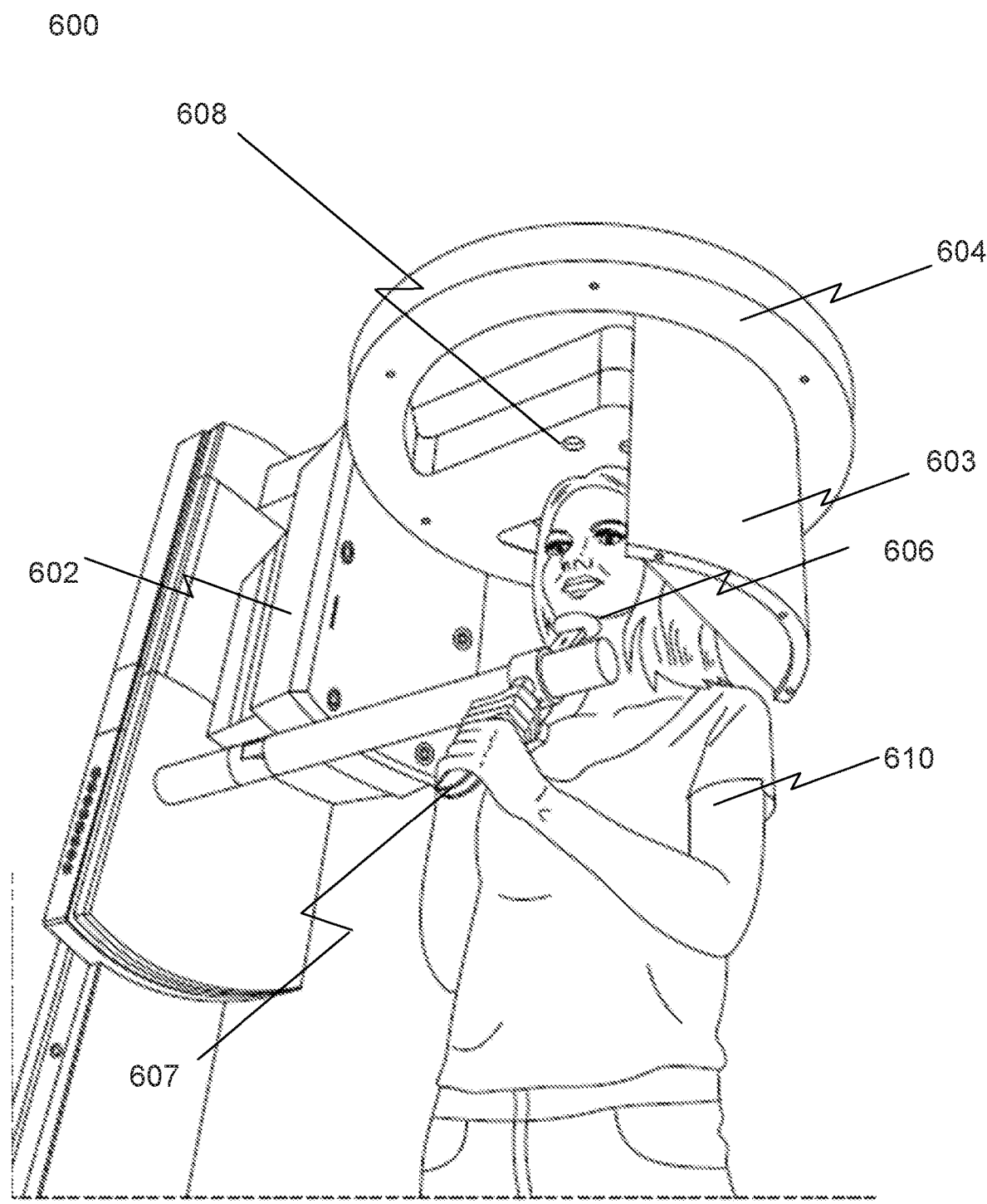
FIG. 6 shows a view of the placement of the cameras in the scanning system according to embodiments of the invention.

FIG. 6 shows a view of the scanning system 600 which illustrates a possible positioning of the cameras 608 according to aspects and embodiments of the invention. The scanning system comprises a base structure, 601, which may be attached to a wall. The scanning system further comprises a radiation source 602, a radiation sensor 603, the radiation source and sensor being attached to or part of a movable ring 604. The scanning system may also comprise a chin rest 606 and a handle 607. The scanning system 600 also comprises at least one camera 608, in this illustration 3 cameras 608, placed so that the cameras have a fixed spatial relationship with respect to the sensor and radiation source. The scanner system 600 is configured to scan an object, in this case a person 610. An integrated or external computer processor (not shown) may also be considered a part of the scanning system. This placement of the cameras may be used in all the embodiments described above and below, but it is not the only possible positioning of the cameras. For example, the cameras may instead be attached to the structure around the radiation source 602, on or around the sensor 603, or another position around the ring 604. An advantage of the placement of the cameras 608 in the center of the movable ring 604 as illustrated here, is that the system can be made more compact. There is no need to add external fixtures to the scanning system for holding the cameras, since the cameras 608 are integrated in the ring structure 604. Therefore, the construction of the scanning system may be simplified. Also, in this configuration, the cameras and the tracking element, typically placed on the top of the head of the person 610, are not within the field of view of the x-ray source/sensor system. This means that there is a more free choice in the materials used for the tracking element.

Although the disclosure of this invention has shown embodiments where the scanner is attached to a wall, the invention and scope of the claims should not be limited to only these embodiments. For example, it is also possible to perform the disclosed methods using free standing scanning systems.

The invention claimed is:

1. A method for determining the position or orientation of at least one sensor system relative to the base structure of a cone beam computed tomography scanning system during scanning of an object, the method comprising:
   obtaining at least three tracking images of a tracking element using at least three camera, where the cameras are in a fixed position with respect to the at least one sensor system; and
   determining from the tracking images the position or orientation of the at least one sensor system relative to the base structure at a given time;
   wherein the determining comprises determining the position or orientation of the tracking element in each of the three tracking images at a time stamp, and computing a weighted average of the position or orientation of the tracking element from the three images.

2. The method according to claim 1, wherein:
   the tracking element is attached in a fixed position with respect to the base structure of the scanning system, the tracking element comprising one or more fiducial markers in a known configuration;
   the tracking images are processed to identify the position of the one or more fiducial markers in a plurality of the tracking images;
   the identified position of the fiducial markers is used to determine the position of the tracking element at a given time; and
   the determined position of the tracking element at a given time is used to determine the movement of the sensor system relative, to the base structure of the scanning system scanned during the acquisition of medical images.

3. The method according to claim 2, wherein the tracking element and cameras define an axis of rotation of the scanner relative to the object being scanned.

4. The method according to claim 1, wherein the determined position or orientation of the at least one sensor system, relative to the base structure of the scanning system, is used to replace positional information from a physical motor encoder.

5. The method according to claim 1, wherein the object being scanned is a person.

6. The method according to claim 1, wherein the method is for determining the position and orientation of the at least one sensor system relative to the base structure of the cone beam computed tomography scanning system during scanning of an object, wherein the determining step includes determining from the tracking images the position and orientation of the sensor system relative to the base structure at a given time.

7. The method according to claim 6, wherein the determined position and orientation of the at least one sensor system, relative to the base structure of the scanning system, is used to replace positional information from a physical motor encoder.

8. A method for determining the position or orientation of at least one sensor system relative to the base structure of a cone beam computed tomography scanning system during scanning of an object, the method comprising:
   obtaining at least three tracking images of a tracking element using at least three cameras, where the cameras are in a fixed position with respect to the sensor system; and determining from the tracking images the position or orientation of the sensor system relative to the base structure at a given time:
   wherein the determining comprises determining the position or orientation of the tracking element in each of the three tracking images at a time stamp, and computing a weighted average of the position or orientation of the tracking element from the three images,
   wherein the at least one sensor system and the cameras are rotated around the object while the tracking images are obtained from the cameras and medical images are obtained from the sensor system.

9. The method according to claim 8, wherein the tracking element is fastened to the object, and the tracking element does not move relative to the base structure while the tracking images are obtained from the cameras and the medical images are obtained from the sensor system.

10. A method for determining the position or orientation of at least one sensor system relative to the base structure of a cone beam computed tomography scanning system during scanning of an object, the method comprising:
- obtaining at least three tracking images of tracking element using at least three cameras, where the cameras are in a fixed position with respect to the sensor system; and
- determining from the tracking images the position or orientation of the sensor system relative to the base structure at a given time;
- wherein the determining comprises determining the position or orientation of the tracking element in each of the three tracking images at a time stamp, and computing a weighted average of the position or orientation of the tracking element from the three images,
- wherein the object is not moved white the tracking images are obtained from the cameras and the medical images are obtained from the at least one sensor system.

11. The method according to claim 10, wherein the sensor system and the cameras are rotated around the object while the tracking images ace obtained from the cameras and medical images are obtained from the sensor system.

12. The method according to claim 11, wherein the tracking element is fastened to the object, and the tracking element does not move relative to the base structure while the tracking images are obtained from the cameras and the medical images are obtained from the sensor system.

\* \* \* \* \*